US00PP28482P3

(12) United States Plant Patent
Suphachadiwong

(10) Patent No.: US PP28,482 P3
(45) Date of Patent: Oct. 3, 2017

(54) ***VANDA* PLANT NAMED 'SPCDW1501'**

(50) Latin Name: ***Vanda* spp. Jones ex R. Br.**
Varietal Denomination: SPCDW1501

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 65 days.

(21) Appl. No.: 14/998,798

(22) Filed: Feb. 17, 2016

(65) Prior Publication Data

US 2016/0242345 P1 Aug. 18, 2016

(30) Foreign Application Priority Data

Feb. 17, 2015 (QZ) ..... PBR 2015/0384

(51) Int. Cl.
*A01H 5/02* (2006.01)

(52) U.S. Cl.
USPC ..... Plt./311

(58) Field of Classification Search
USPC ..... Plt./263.1, 311
See application file for complete search history.

*Primary Examiner* — Susan McCormick Ewoldt
*Assistant Examiner* — Karen Redden
(74) *Attorney, Agent, or Firm* — Samuel R. McCoy, Jr.

(57) ABSTRACT

A new and distinct *Vanda* cultivar named 'SPCDW1501' which is characterized by sepals and petals with a unique color combination of light purple and blue and heavily dotted and blotched with dark purple, as well as a very dark purple labellum contrasting the petals and sepals, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1501'.

CROSS REFERENCE TO RELATED APPLICATIONS

This application claims priority to the Community Plant Variety Rights application number 2015/0384, filed Feb. 17, 2015, which is herein incorporated by reference.

BACKGROUND OF THE INVENTION

Parentage: The *Vanda* variety 'SPCDW1501' is the result of a planned breeding program. The new variety originated as a seedling from the crossing of the unpatented, proprietary seed parent *Vanda* 'T131B' with the unpatented, proprietary pollen parent *Vanda* 'T9112'. Both parents were developed by, and are owned by, the inventor and were never commercially released. The crossing was made by the inventor in his research greenhouse in Bangphra, Thailand in April of 2004.

The new variety was first selected in June of 2008, in a research greenhouse in Bangphra, Thailand belonging to the inventor. After identifying the new variety as a potentially interesting selection, the inventor continued confidential testing and propagation of 'SPCDW1501', assessing stability of the unique characteristics of this variety.

Asexual Reproduction: Asexual reproduction of the new cultivar 'SPCDW1501', by way of mericloning, was first initiated in April of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1501' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1501'. These characteristics in combination distinguish 'SPCDW1501' as a new and distinct *Vanda* cultivar:

1. *Vanda* 'SPCDW1501' exhibits sepals and petals with a unique color combination of light purple color and blue; and
2. *Vanda* 'SPCDW1501' exhibits sepals and petals that are heavily dotted and blotched with dark purple; and
3. *Vanda* 'SPCDW1501' exhibits a very dark purple general tonality of the labellum's central lobe.

BOTANICAL DESCRIPTION OF THE PLANT

Figure 1:
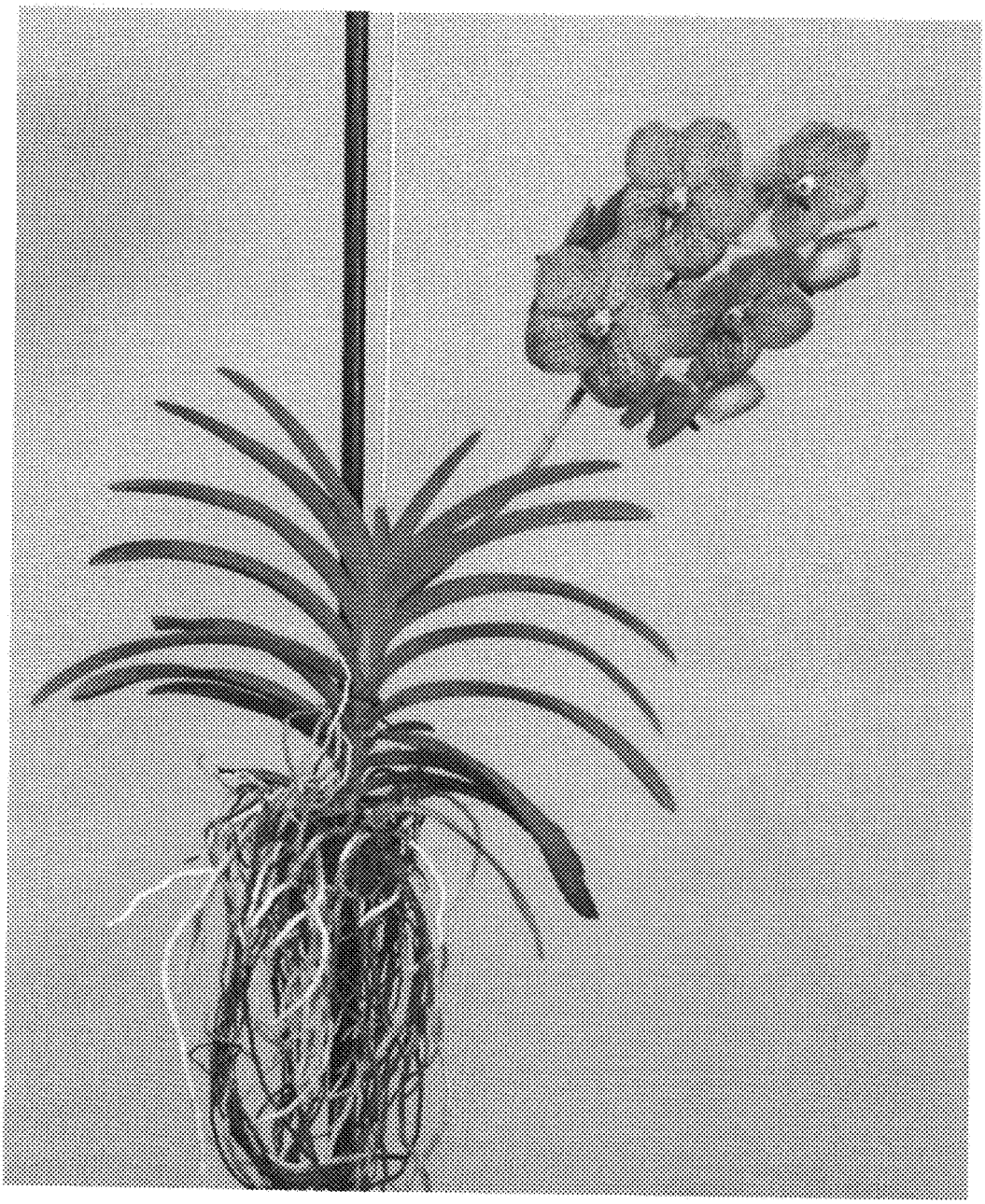
FIG. 1 illustrates, as nearly true as it is reasonably possible to make the same in color photographs of this type, an exemplary plant of 'SPCDW1501' grown in a commercial greenhouse in Honselersdijk, the Netherlands. This plant is approximately 6 years old from the time of mericloning, shown planted in an 8 by 8 cm container.
Figure 2:
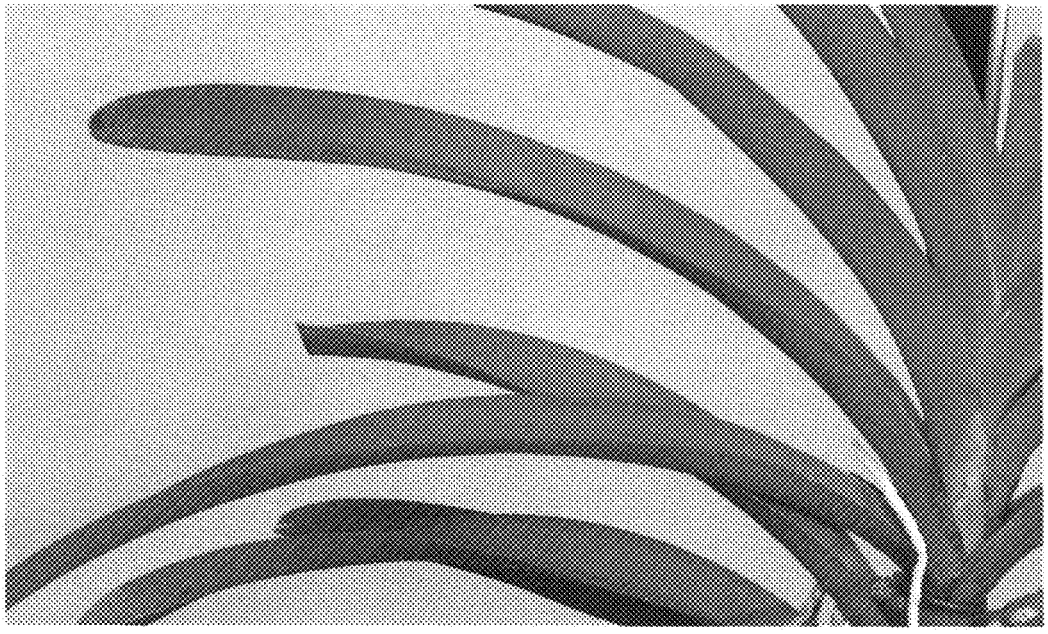
FIG. 2 illustrates, as nearly true as it is reasonably possible to make the same in color photographs of this type, the typical foliage of 'SPCDW1501'.
Figure 3:
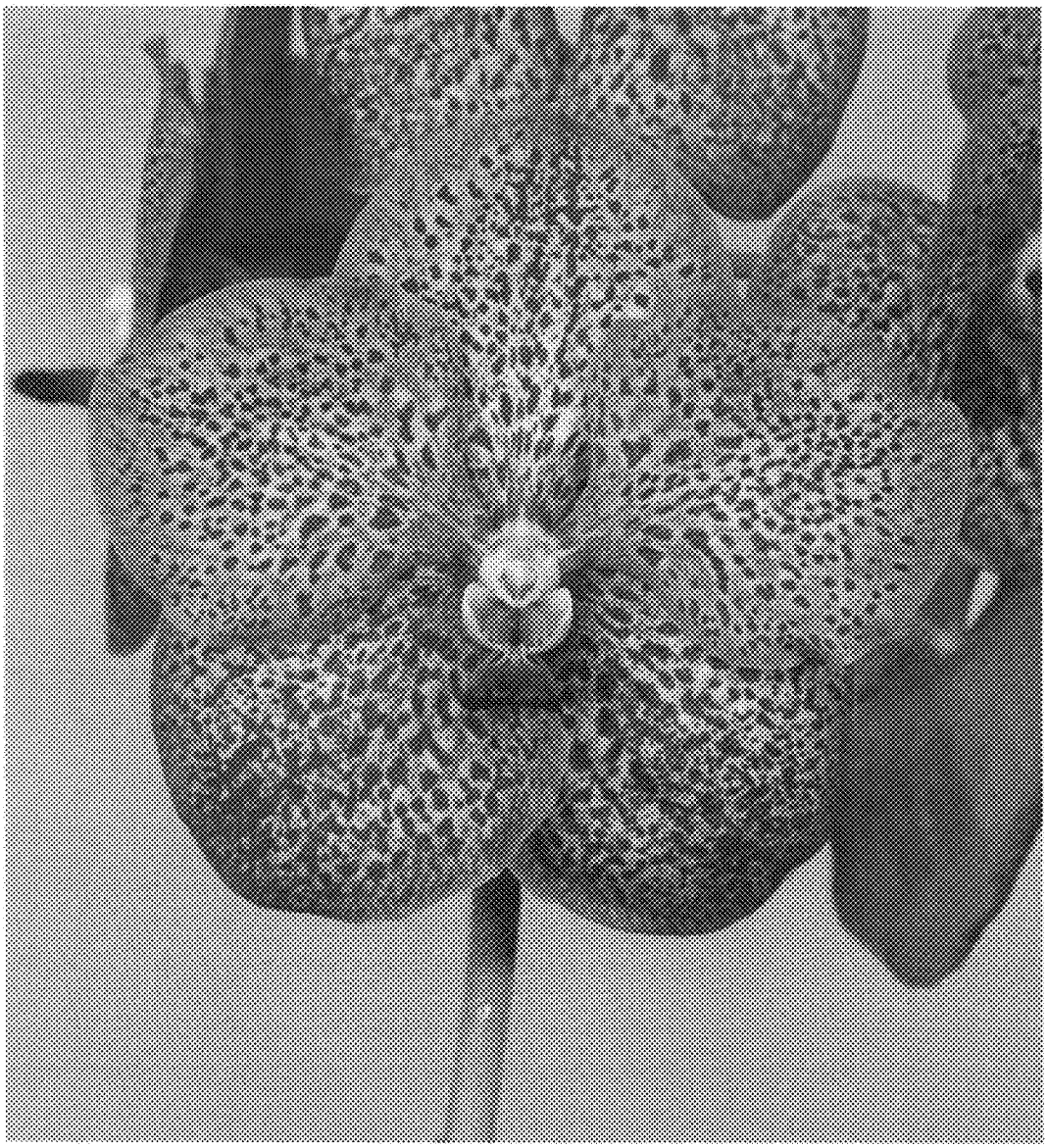
FIG. 3 illustrates, as nearly true as it is reasonably possible to make the same in color photographs of this type, the typical flower of 'SPCDW1501'.
Figure 4:
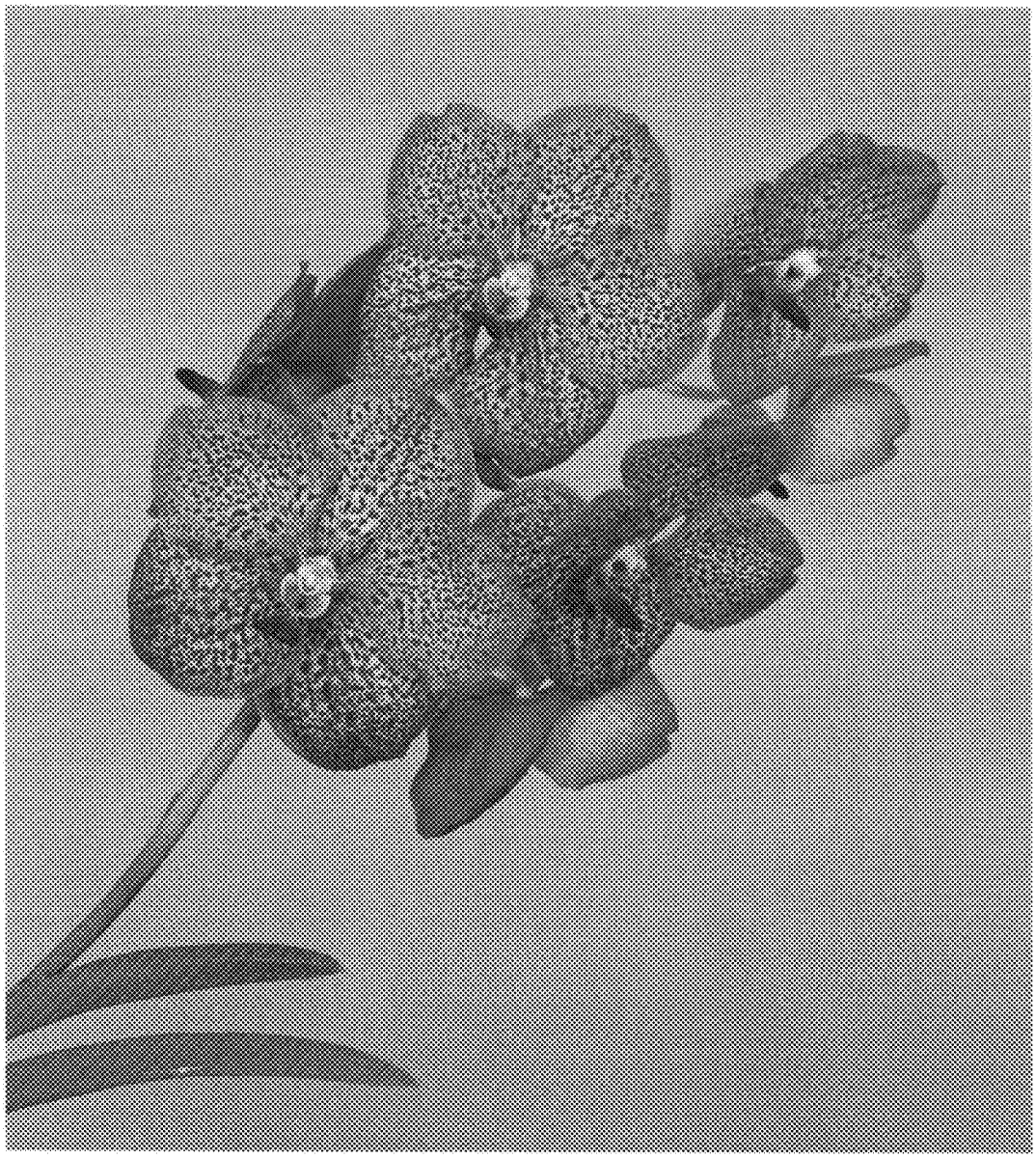
FIG. 4 illustrates, as nearly true as it is reasonably possible to make the same in color photographs of this type, the typical inflorescence of 'SPCDW1501'.

The following observations and measurements made in January of 2016 describe averages from a sample set of six specimens of six year-old 'SPCDW1501' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1501' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1501' and comparisons with other varieties of *Vanda* are provided below.

Plant description:

- *Growth habit.*—Perennial; monopodial, upright. Single monopodial leafy stem, with flowers carried slightly above the leaf plane, inflorescences grow from the leaf axils.
- *Average height from base (plant grown in hanging basket, so no soil line present) to top of foliage.*—30.0 cm.
- *Average height from base (plant grown in hanging basket, so no soil line present) to top of floral plane.*—51.8 cm.
- *Plant spread.*—Average of 40.8 cm.
- *Normal pot size.*—Hanging basket (8 by 8 cm, square).
- *Growth rate.*—Moderate.
- *Plant vigor.*—Moderate.
- *Propagation type.*—Tissue culture propagation using the base of the leaves.
- *Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility.*—Similar to other *Vanda* varieties.
- *Environmental tolerances.*—Adapt to, at least, USDA Zones 11 and 12 and temperatures as high as 40 degrees Celsius; high tolerance to rain; moderate to high tolerance to wind.

Root system:

- *General.*—Densely rooting; with aerial roots only.
- *Dimensions, mature roots.*—59.4 cm long with a diameter of 0.4 cm. on average.
- *Texture.*—Very fleshy; non-fibrous.
- *Color.*—Greyed-Green, near RHS 192B to 192C; root apex is yellow-green, RHS 147B to 147C.

Stem:

- *Branching habit.*—Monopodial; no lateral branches present.
- *Number of primary (main) stems per plant.*—One.
- *Number of secondary (lateral) branches per plant.*—None.
- *Appearance and shape.*—Circular, formed by the leaf sheaths.
- *Length.*—16.0 cm.
- *Diameter.*—1.0 cm.
- *Internode length.*—0.4 cm.
- *Luster.*—Matte.
- *Aspect.*—Near vertical.
- *Strength.*—Very strong.
- *Color, juvenile.*—Yellow-green, near RHS 145B.
- *Color, mature.*—Yellow-green, near RHS 145B.
- *Color at internodes.*—Yellow-green, near RHS 145B.
- *Pubescence.*—Glabrous.

Foliage:

- *Arrangement.*—Distichous.
- *Quantity.*—Approximately 22 leaves per plant.
- *Dimensions.*—22.1 cm long and 2.1 cm wide, on average.
- *Shape of blade.*—Ligulate; moderately to strongly carinate.
- *Aspect.*—Moderately curved.
- *Apex.*—Unequal praemorse.
- *Base.*—Sheathing.
- *Sheath dimensions.*—3.0 cm long and 1.2 cm wide, on average.
- *Sheath color.*—Yellow-green, in between RHS 144A and 145A.
- *Margin.*—Entire.
- *Pubescence, texture and luster of adaxial surface.*—Glabrous, smooth, and very slightly glossy.
- *Pubescence, texture and luster of abaxial surface.*—Glabrous, smooth, and matte.
- *Color.*—Juvenile foliage, adaxial surface — Green, near RHS 143B, and darker towards the margins, near 143A. Juvenile foliage, abaxial surface — Green, near RHS 143A to 143B. Mature foliage, adaxial surface — Green, in between RHS 137B and 143A; closest to 137B. Mature foliage, abaxial surface — Green to yellow-green, in between RHS 143A and 146B.
- *Venation.*—Parallel.
- *Venation color, adaxial surface.*—Green, in between RHS 137B and 143A; closest to 137B.
- *Venation color, abaxial surface.*—Green RHS 143A.
- *Petiole.*—No petioles present, leaves sessile.

Inflorescence:

- *Inflorescence arrangement.*—Axially placed raceme.
- *Natural flowering season.*—Autumn into winter.
- *Time to flower.*—Approximately 10 months.

*Flowers per inflorescence.*—Average of 9; 8 open flowers and 1 bud.

*Inflorescence height.*—Approximately 25.2 cm (measured from base of lowest flower to top of upper flower).

*Inflorescence diameter.*—Approximately 19.5 cm.

*Peduncle.*—Dimensions — Approximately 39.8 cm long and 0.6 cm wide. Aspect — Generally at a 35 degree angle to lateral branch axis; ranging from 20 degrees to 50 degrees to lateral branch axis. Strength — Moderately strong. Texture and luster — Glabrous and moderately glossy. Color — Green, RHS 143A.

Bud:

*Length.*—Average of 1.3 cm.

*Diameter.*—Average horizontal diameter is 1.2 cm; the vertical diameter is 1.3 mm.

*Shape.*—Cubic, with a deltoid apex which is pointed downward.

*Pubescence, texture and luster.*—Glabrous, smooth and moderately glossy.

*Color.*—Yellow-green, near RHS 144D; apex is greyed-purple, near RHS N187B.

Flower:

*Flower type.*—Zygomorphic (orchidaceous), typical shape for the genus *Vanda*.

*Flowering habit.*—Moderate.

*Shape.*—Zygomorphic, single; consisting of three sepals and three petals, one of which is transformed into a labellum.

*Aspect.*—Flowers are outward-facing to slightly nodding.

*Vertical height.*—Approximately 11.2 cm.

*Diameter.*—Approximately 11.3 cm.

*Depth.*—Approximately 4.0 cm.

*Fragrance.*—No fragrance.

*Lastingness.*—3 weeks, on average.

*Persistent.*—Self-cleaning.

*Petals.*—Quantity of Petals — 3 unfused petals; two conventional petals and one labellum. Arrangement — One lateral petal on each side. Length — Approximately 5.5 cm. Width — Approximately 5.4 cm. Shape — Near orbicular. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — White, near NN155A, and fading to violet, near N88D, towards the apex; petals are moderately to heavily dotted violet-blue, RHS N92A. Color when opening, lower surface — White, near NN155A, and fading to violet, near N88D, towards the apex; dots from upper surface can be seen from the lower surface; near RHS N92A. Color when fully opened, upper surface — Violet, near RHS N88C, and margined slightly darker, in between RHS N88B to N88C; petals are heavily dotted and blotched violet, near RHS 86A, to violet-blue, near RHS N92A; dots and blotches are margined lighter, near RHS 85B to 85C. Color when fully opened, lower surface — Violet-blue, near RHS 90D, and fading to violet towards the apex, in between N88B and N88C. Fading, upper surface — Not fading. Fading, lower surface — Not fading. Venation — Reticulate. Venation color, fully opened, upper surface — Violet, near RHS N88C, and margined slightly darker, in between N88B and N88C. Venation color, fully opened, lower surface — Violet-blue, near RHS 90C, and fading to violet towards the apex, in between N88B and N88C.

*Labellum.*—Shape — Three-lobed, lateral lobes involute, central lobe revolute. Length — Central lobe — Approximately 2.1 cm. Lateral lobes — Approximately 0.9 cm. Width — Central lobe — Approximately 1.2 cm. Lateral lobes — Approximately 0.7 cm. Apex, central lobe — Emarginate. Apex, lateral lobes — Obtuse. Base, central and lateral lobes — Cuneate. Margin, central lobe — Entire; not undulate. Margin, lateral lobes — Irregularly dentate; slightly undulate. Texture and luster of upper surface — Central lobe — Glabrous, velvety, and very slightly glossy. Lateral lobes — Glabrous, velvety, and matte. Texture and luster of lower surface — Central lobe — Glabrous, velvety, and very slightly glossy. Lateral lobes — Glabrous, velvety, and matte. Color when opening, upper surface — Central lobe — Violet, near RHS 87A. Lateral lobes — Greyed-yellow, near RHS 160D and lighter; striped violet at the base, near RHS N87B and N87C. Color when opening, lower surface — Central lobe — Violet, near RHS 87B, and lighter towards the base, near RHS 85A. Lateral lobes — White, near RHS 155A, and striped violet at the base, near RHS N87C. Color when fully opened, upper surface — Central lobe — Violet, near RHS 86A, and violet-blue at the apex, near RHS N92C. Lateral lobes — Violet, near RHS 85A, and striped violet at the base, near RHS N87B and N87C, with a yellow dot at the base, near 8A. Color when fully opened, lower surface — Central lobe — Violet-blue, near RHS N92A; lighter towards the base, RHS 90C. Lateral lobes — Violet, closest to a combination of N87D and N88D, and lighter. Fading, upper surface — Not fading. Fading, lower surface — Not fading. Venation — Reticulate. Venation color, fully opened, upper surface — Central lobe — Violet, near RHS 86A; apex is violet-blue near N92C. Lateral lobes — Violet, near RHS 85A, and striped violet at the base, near RHS N87B and N87C, with a yellow dot at the base, near 8A. Venation color, fully opened, lower surface — Central lobe — Violet-blue, near RHS N92A; lighter towards the base, RHS 90C. Lateral lobes — Violet, closest to a combination of RHS N87D and N88D, and lighter.

*Callosities.*—Dimensions — 1.7 cm long and 0.7 cm wide, on average. Color — Violet, near RHS N88C and N88D.

*Spurs.*—Quantity — Average of 1. Length — Approximately 0.7 cm. Diameter — Approximately 0.4 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Violet, near RHS 85D, and striped darker, near 85A.

*Sepals.*—Quantity — Average of 3 unfused sepals. Arrangement — One dorsal sepal and two lateral sepals. Length — Dorsal sepal — Approximately 5.7 cm. Lateral sepals — Approximately 6.0 cm. Width — Dorsal sepal — Approximately 5.4 cm.

Lateral sepals — Approximately 6.5 cm. Shape — Dorsal sepal — Broad ovate. Lateral sepals — Reniform to near orbicular. Apex, dorsal and lateral sepals — Obtuse. Base, dorsal and lateral sepals — Cuneate. Margin, dorsal and lateral sepals — Entire; all sepals are slightly undulate. Pubescence, texture and luster — Glabrous, velvety, and matte on both the upper and lower sepal surfaces. Color when opening, upper surface — Both dorsal and lateral sepals are white, near RHS NN155A, and fading to violet towards the apex, near RHS N88D. On lateral sepals, the central area of the sepal surface is violet, near RHS N88D. All sepals are moderately to heavily dotted violet-blue, RHS N92A. Color when opening, lower surface — The dorsal sepal is white, near RHS NN155A, and fading to violet towards the apex, near RHS N88D, with the violet-blue dots of the upper surface visible on the lower surface, near N92A. Lateral sepals are white, near RHS NN155A, and fading to violet towards the apex, near RHS N88C to N88D. Color when fully opened, upper surface — Both dorsal and lateral sepals are violet, near RHS N88C, and margined slightly darker, in between RHS N88B to N88C. All sepals are heavily dotted and blotched violet and violet-blue, near RHS 86A and N92A; dots and blotches are margined lighter, near RHS 85B to 85C. Dots on lateral sepals are larger and more numerous than those of the dorsal sepal. Color when fully opened, lower surface — Both dorsal and lateral sepals are violet-blue, near RHS 90D, and fading to violet towards the apex, in between N88B and N88C. Fading, upper surface — The color of all sepals does not fade. Fading, lower surface — The color of all sepals docs not fade. Venation — Reticulate. Venation color, fully opened, upper surface — Both dorsal and lateral sepals are violet, near RHS N88C, and margined slightly darker, closest to a combination of N88B and N88C. Veins of all sepals are heavily dotted and blotched violet and violet-blue, near RHS 86A and N92A; dots and blotches are margined lighter, near RHS 85B and 85C. Dots on lateral sepals are larger and more numerous than those of the dorsal sepal. Venation color, fully opened, lower surface — Both dorsal and lateral sepals are violet-blue, in between RHS N88B and N88C.

*Pedicels.*—Length — Approximately 6.3 cm. Diameter — Approximately 0.5 cm. Angle — Approximately 80 degree angle to peduncle axis. Strength — Moderate. Texture — Glabrous, axially angled with 5 "ribs", axially twisted (due to resupination). Luster — Glossy. Color — Violet, near RHS N87D and lighter; slightly tinged yellow-green RHS 147C towards the proximal end.

*Bract.*—Quantity — One bract present at the base of each pedicel. Shape — Reniform; folded around the base of each pedicel. Dimensions — Average of 1.1 cm long and 1.8 cm wide. Apex — Broad acute. Base — Broad Cuneate. Margins — Entire. Color, both surfaces — Yellow-green, near RHS 144C.

Reproductive organs:

*Column.*—Length — Approximately 0.5 cm. Diameter — Approximately 0.7 cm. Color — White RHS 155C; upper side is purple-violet RHS N82B.

*Ovary.*—Position — Inferior. Diameter — Approximately 1.1 cm. Color — Yellow-green RHS 150B.

*Pollinia color.*—Yellow-orange RHS 15A.

Seed and fruit: No fruit and seed production has been detected to date.

COMPARISONS WITH THE PARENT PLANTS

Plants of the new cultivar 'SPCDW1501' are similar to the seed parent, *Vanda* 'T131B', in most horticultural characteristics. However 'SPCDW1501' differs from the seed parent in the fallowing characteristics:

1. 'SPCDW1501' has a more compact growth habit when compared to that of 'T131B'.
2. The general flower color of 'SPCDW1501' is darker purple when compared to 'T131B'.
3. 'SPCDW1501' exhibits smaller flowers than those of 'T131B'.
4. 'SPCDW1501' is more free-flowering compared to 'T131B'.

Plants of the new cultivar 'SPCDW1501' are similar to the pollen parent, *Vanda* 'T9112', in most horticultural characteristics. However 'SPCDW1501' differs from the pollen parent in the following characteristics:

1. The flowers of 'SPCDW1501' are not as heavily dotted and blotched with dark purple as the flowers of 'T9112'.
2. The flowers of 'SPCDW1501' are larger than the flowers of 'T9112'.
3. 'SPCDW1501' exhibits more vigor and a faster growth rate when compared to 'T9112'.

COMPARISON WITH THE MOST SIMILAR *VANDA* CULTIVAR KNOWN TO THE INVENTOR

A comparison of 'SPCDW1501' with the most similar *Vanda* cultivar known to the inventor, *Vanda* 'Princess Mikasa' (not patented), is described in Chart 1.

CHART 1

| Characteristic | 'SPCDW1501' | 'Princess Mikasa' |
|---|---|---|
| Average foliage width | 2.1 cm. | 2.3 cm. |
| Average flower dimensions | Vertical height is 11.2 cm; diameter is 11.3 cm. | Vertical height is 9.3 cm; diameter is 9.2 cm. |
| General coloration of petals when opening. | White, fading to violet; heavily dotted violet-blue. | Violet; lower part of petal finely dotted violet. |
| General coloration of petals when fully open. | Violet to violet-blue; heavily dotted and blotched violet and violet-blue. | Generally violet. |
| Length of labellum | Lateral lobes 0.9 cm; central lobe 2.1 cm. | Lateral lobes 0.6 cm; central lobe 1.9 cm. |
| Labellum apices | Lateral lobes obtuse; central lobe emarginate. | Lateral lobes emarginate; central lobe strongly emarginate. |
| Labellum, central lobe coloration when fully open | Upper surface violet, with apex violet-blue; lower surface violet-blue and lighter, violet, towards the base. | Upper surface violet-blue and slightly lighter at the base, violet; lower surface violet and lighter towards the base. |
| Average sepal dimensions | Dorsal sepal is 5.7 cm long and 5.4 cm wide; lateral sepals are 6.0 cm long and 6.5 cm wide. | Dorsal sepal is 4.6 cm long and 4.0 cm wide; lateral sepals are 4.9 cm long and 4.6 cm wide. |

CHART 1-continued

| Characteristic | 'SPCDW1501' | 'Princess Mikasa' |
|---|---|---|
| General coloration of sepals when opening. | White, fading to violet towards apex; central portion of lateral sepals violet; all sepals heavily dotted violet-blue. | All sepals are violet; veins darker. |
| General coloration of sepals when fully open. | Violet and margined slightly darker on upper surface and margined lighter on the lower surface; all sepals heavily dotted and blotched violet and violet-blue on upper surface; dots on lateral sepals more numerous than those of the dorsal sepal. | All sepals are violet. |
| Sepal venation color, when fully open. | Violet and margined slightly darker on upper surface; violet-blue and fading to violet towards the apex on the lower surface; all sepals heavily dotted and blotched violet and violet-blue on upper surface; dots on lateral sepals more numerous than those of the dorsal sepal. | All sepals are violet. |
| Spur dimensions and shape | 0.7 cm long with a horizontal diameter of 0.1 cm and vertical height of 0.7 cm; short triangular. | 0.8 cm long with a horizontal diameter of 0.25 cm and vertical height of 0.5 cm; flattened, narrow triangular. |

That which is claimed is:

1. A new and distinct variety of *Vanda* plant named 'SPCDW1501', substantially as described and illustrated herein.

* * * * *